US009999522B2

United States Patent
Gill

(10) Patent No.: US 9,999,522 B2
(45) Date of Patent: Jun. 19, 2018

(54) PROSTHETIC DIGIT FOR USE WITH TOUCHSCREEN DEVICES

(71) Applicant: TOUCH BIONICS LIMITED, Livingston (GB)

(72) Inventor: Hugh Gill, Paisley Strathclyde (GB)

(73) Assignee: Touch Bionics Limited, Livingston (GB)

( * ) Notice: Subject to any disclaimer, the term of this patent is extended or adjusted under 35 U.S.C. 154(b) by 0 days. days.

(21) Appl. No.: 15/120,784

(22) PCT Filed: Feb. 6, 2015

(86) PCT No.: PCT/GB2015/050337
§ 371 (c)(1),
(2) Date: Aug. 23, 2016

(87) PCT Pub. No.: WO2015/128604
PCT Pub. Date: Sep. 3, 2015

(65) Prior Publication Data
US 2017/0007424 A1    Jan. 12, 2017

(30) Foreign Application Priority Data
Feb. 25, 2014 (GB) .................................. 1403265.0

(51) Int. Cl.
*A61F 2/54*    (2006.01)
*G06F 3/041*    (2006.01)
*A61F 2/58*    (2006.01)
*A61F 2/68*    (2006.01)
(Continued)

(52) U.S. Cl.
CPC ................ *A61F 2/586* (2013.01); *A61F 2/68* (2013.01); *A61F 2/70* (2013.01); *G06F 3/0416* (2013.01); *A61F 2002/5038* (2013.01); *A61F 2002/5072* (2013.01); *A61F 2002/701* (2013.01); *A61F 2240/001* (2013.01)

(58) Field of Classification Search
CPC ............. A61F 2/54; A61F 2/583; A61F 2/586
See application file for complete search history.

(56) References Cited

U.S. PATENT DOCUMENTS

| 8,337,568 | B2 | 12/2012 | MacDuff |
| 8,491,666 | B2 | 7/2013 | Schulz |
| 2011/0278061 | A1 | 11/2011 | Farnan |

(Continued)

FOREIGN PATENT DOCUMENTS

| DE | 102012009699 A1 | 11/2013 |
| WO | 2010051798 A1 | 5/2010 |

OTHER PUBLICATIONS

International Search Report and Written Opinion from PCT/GB2015/050337 dated Apr. 29, 2015.

*Primary Examiner* — Marcia Watkins
(74) *Attorney, Agent, or Firm* — Knobbe, Martens, Olson & Bear, LLP

(57) ABSTRACT

A digit for a prosthetic hand is provided. The digit has a base member (12) attachable to the hand and at least one digit member (18) pivotably connected to the base member. The at least one digit member (18) has a digit tip (22) remote from the base member (12), and the digit member is at least partially covered with at least one conductive substance (26,40) which defines a conductive path which leads from the digit tip towards the base member. A method of manufacturing such a digit is also provided.

7 Claims, 2 Drawing Sheets

(51) Int. Cl.
　　　*A61F 2/50*　　　(2006.01)
　　　*A61F 2/70*　　　(2006.01)

(56) References Cited

U.S. PATENT DOCUMENTS

| | | |
|---|---|---|
| 2012/0109337 A1 | 5/2012 | Schulz |
| 2012/0303136 A1 | 11/2012 | MacDuff |
| 2013/0076699 A1* | 3/2013 | Spencer .................. G06F 3/039 345/179 |
| 2013/0268094 A1 | 10/2013 | Van Wiemeersch |
| 2014/0236314 A1 | 8/2014 | Van Wiemeersch |

\* cited by examiner

PROSTHETIC DIGIT FOR USE WITH TOUCHSCREEN DEVICES

CROSS REFERENCE TO RELATED APPLICATIONS

This is the national phase under 35 U.S.C. § 371 of International Application No. PCT/GB2015/050337, filed on Feb. 6, 2015, which claims priority to and the benefit of Great Britain Patent Application No. 1403265.0, filed on Feb. 25, 2014, the entire disclosures of each of which are incorporated by reference herein.

FIELD OF THE INVENTION

The present invention is directed to the field of prosthetics and orthotics, and in particular a hand prosthetic. More specifically the present invention is directed to digits used on prosthetic hands, and to a digit which will allow the wearer to operate a touchscreen device with such a digit.

BACKGROUND OF THE INVENTION

Many amputees and partial amputees now wear prosthetic hands incorporating powered and/or non-powered digits. As mobile telephone and device technology has developed in recent years, many of those persons now own a mobile telephone, tablet or other device which has a touchscreen. The touchscreens in the majority of these devices detect a user's input using sensors and circuitry to monitor changes in a particular state of the screen. Many of these devices employ capacitive touchscreens which use a layer of capacitive material to hold an electrical charge, and when the user's finger touches the screen the capacitance at the point of contact changes, thereby indicating at which point the user is touching the screen.

The digits of hand prosthetics are typically formed from stainless steel or a similar metal and are usually covered by some form of protective and/or aesthetic cover formed from an elastomer. The elastomer layer may or may not be covered in certain areas by polyurethane or the like so as to aid donning and removal of the cover. The presence of such covers presents a problem to a prosthetic wearer who wishes to operate the aforementioned touchscreens, as the cover interferes with the ability of the user to change the capacitance when touching the touchscreen. Prosthetic wearers who still have one hand can choose to operate the device with that hand, but this can be inconvenient and is obviously not an option for those who have lost both hands.

It has been established that simply removing the cover from the digit and using the metal digit to touch the screen does not change the capacitance as needed. One solution which has been proposed has been to provide a metal pad or dome at the tip of the digit. However, it has been found that the success of this arrangement is dependent on the specific shape of the contact surface on the digit and also this very often leads to scratching and cracking of the relatively delicate screen after frequent sweeping and tapping motions by the metal pad. Another proposal has been to provide conductive threads in the digit covers, with the threads running along the length of the cover from the tip. However it has been found that repeated folding and extending motions of the digits can cause these threads to wear and break relatively quickly, thereby preventing the required change in capacitance. A further solution has been to connect the digit tip to an external conductive wire. However, running a conductive wire down the entire length of the digit increases the likelihood of the wire fouling upon another component or object or accelerating fatigue in the wire as it is stretched every time the digit is closed, with the result being an increased likelihood of damage to, or failure of, the conductive wire.

It is an aim of the present invention to obviate or mitigate one or more of these disadvantages.

SUMMARY OF THE INVENTION

According to a first aspect of the invention there is provided a digit for a prosthetic hand, the digit comprising:
  a base member attachable to the hand; and
  at least one digit member pivotably connected to the base member;
  wherein the at least one digit member has a digit tip remote from the base member, and the digit member is at least partially covered with at least one conductive substance which defines a conductive path which leads from the digit tip towards the base member.

The digit may further comprise a cover adapted to fit over at least the digit tip, the cover having a cover tip which lies over the digit tip when the cover is in place, wherein the cover tip includes at least one aperture extending through the cover, and the at least one conductive substance is provided on an exterior of the cover tip and within the at least one aperture such that it defines part of the conductive path from the exterior of the cover tip to the digit tip.

The at least one conductive substance may be selected from the group comprising: a conductive adhesive, a conductive paint and a conductive coating.

Alternatively, the digit tip may be at least partially covered with a first conductive substance, and an adjacent portion of the at least one digit member is at least partially covered with a second conductive substance, the first and second conductive substances defining the conductive path.

The first conductive substance may be a conductive adhesive, and the second conductive substance may be a conductive paint.

The digit may further comprise:
  a first digit member pivotably connected to the base member;
  a second digit member pivotably connected to the first digit member, the second digit member including the digit tip at a remote end thereof; and
  a biasing member having a first end connected to the first digit member and a second end connected to the second digit member, the biasing member biasing the second digit member towards substantial alignment with the first digit member;
  wherein the at least one conductive substance is provided on the second digit member, and the biasing member extends the conductive path from the second digit member to the first digit member.

The digit may be a powered digit and further comprise a motor contained within a motor casing, and a conductive wire having a first end connected to the first end of the biasing member, and a second end connected to the motor casing.

According to a second aspect of the invention there is provided a method of manufacturing a digit for a prosthetic hand, the method comprising the steps of:
  pivotably connecting at least one digit member to a base member which is attachable to the hand, the digit member having a digit tip which is remote from the base member; and at least partially covering the at least one digit member with at least one conductive substance which defines a conductive path which leads from the digit tip towards the base member.

The method may further comprise the steps of:
providing a cover to cover at least the digit tip, the cover having a cover tip which lies over the digit tip when in use;
forming at least one aperture in the cover tip such that the aperture extends through the cover;
inserting a portion of the at least one conductive substance into the at least one aperture such that the conductive substance is provided on an exterior of the cover tip and within the at least one aperture; and
fitting the cover over the digit tip, such that the at least one conductive substance defines part of the conductive path from the exterior of the cover tip to the digit tip.

The at least one conductive substance may be selected from the group comprising: a conductive adhesive, a conductive paint, a conductive coating and a conductive film.

Alternatively, the method may further comprise the steps of:
at least partially covering the digit tip with a first conductive substance; and
at least partially covering an adjacent portion of the at least one digit member with a second conductive substance;
wherein the first and second conductive substances define the conductive path.

The first conductive substance may be a conductive adhesive, and the second conductive substance may be a conductive paint.

The method may further comprise the steps of:
forming first and second digit members, wherein the second digit member includes the digit tip at a remote end thereof and the at least one conductive substance is provided on the second digit member;
pivotably connecting the first digit member to the base member;
pivotably connecting the second digit member to the first digit member; and
connecting a first end of a biasing member to the first digit member and a second end of the biasing member to the second digit member, such that the biasing member biases the second digit member towards substantial alignment with the first digit member, and the biasing member extends the conductive path from the second digit member to the first digit member.

The method may further comprise the steps of:
providing the digit with a motor contained within a motor casing;
connecting a first end of a conductive wire to the first end of the biasing member; and
connecting the second end of the conductive wire to the motor casing.

BRIEF DESCRIPTION OF THE DRAWINGS

A preferred embodiment of the present invention will now be described, by way of example only, with reference to the following drawings.

DETAILED DESCRIPTION OF THE DRAWINGS

Figure 1:
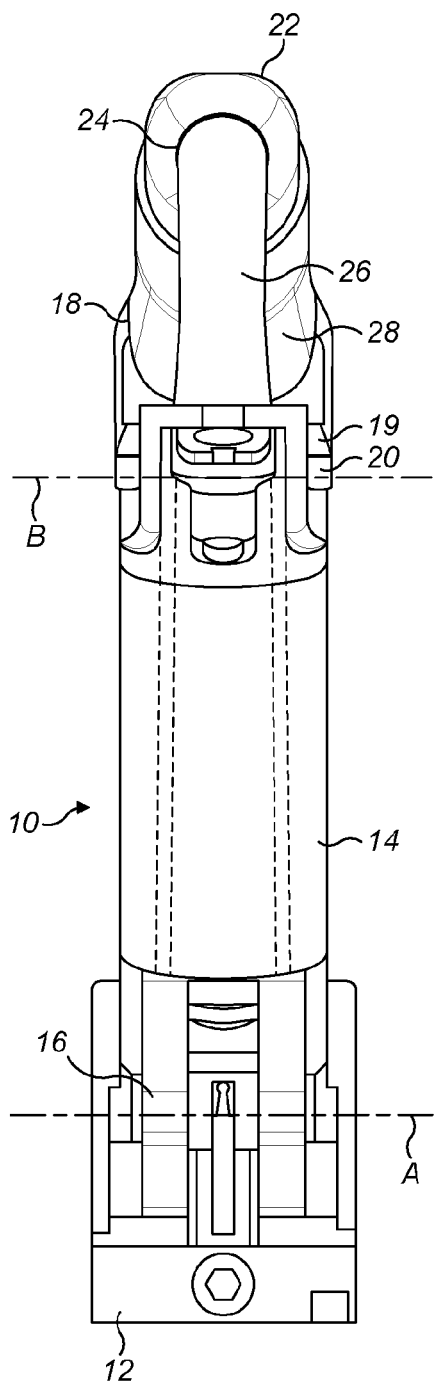
FIG. 1 is a front view of a digit for a prosthetic hand.

FIG. 1 shows a front view of a digit 10 for use in a prosthetic hand of an amputee or partial amputee. The present invention may be applied to both powered and non-powered digits, but for the purposes of this example the digit is powered.

The digit may be formed from aluminium, stainless steel or another ferrous metal which allows conduction. Alternatively, the digit may be formed from a plastics material. The digit 10 comprises a base or support member 12 which allows the digit 10 to be secured to a hand chassis or mount (not shown) which is attached to the hand or residual stump of the wearer in a known manner. A first digit member 14 is connected to the base member 12 about a first, or proximal, pivot rod 16 which allows the first digit member 14 to pivot about a rotational axis A of the first rod 16 relative to the base member 12. A second digit member 18 is connected to a distal end of the first digit member 14 about a second, or distal, pivot rod 20 which allows the second digit member 18 to pivot about a rotational axis B of the second rod 20 relative to the first digit member 14. The second digit member 18 includes a tip 22 at the end of the second digit member 18 which is remote from the second rod 20. The tip 22 may include a flattened surface 24 which is intended to replicate the pad of a human fingertip. An electrically conductive paint or coating 26 is applied to the tip 22 and front face 28 (that is, the face of the second digit member 18 facing the viewer in FIG. 1) of the second digit member 18 so as to create a conductive track or path from the tip 22 to a proximal end 19 of the second digit member 18. A non-limiting example of a paint or coating suitable for this purpose is "Silver Conductive Paint" sold by RS Components Limited of Corby, United Kingdom. This paint has a silver content of 35-65%.

Figure 2:
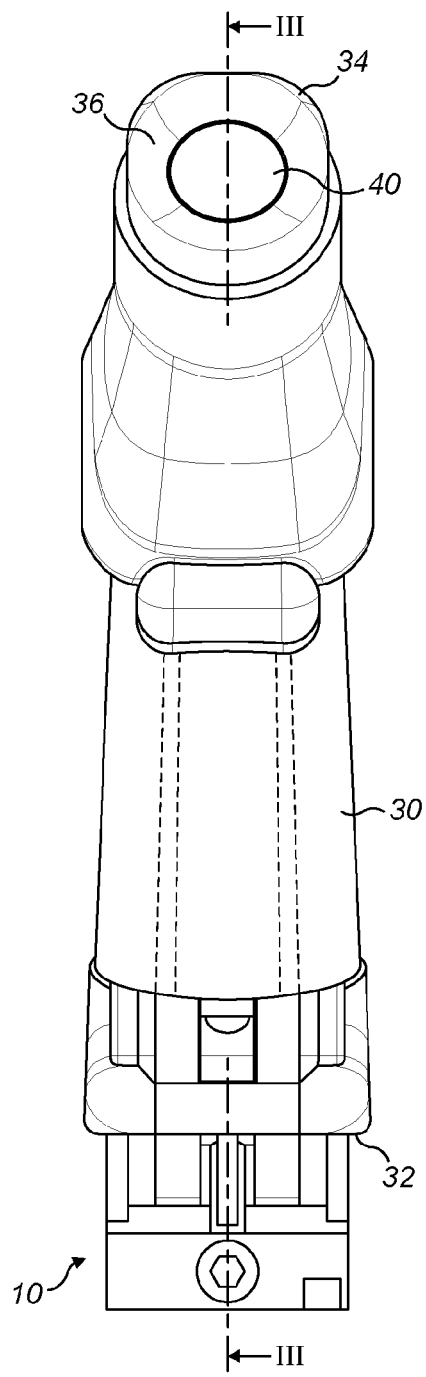
FIG. 2 is a front view of the digit shown in FIG. 1 with a protective cover over the digit.
Figure 3:
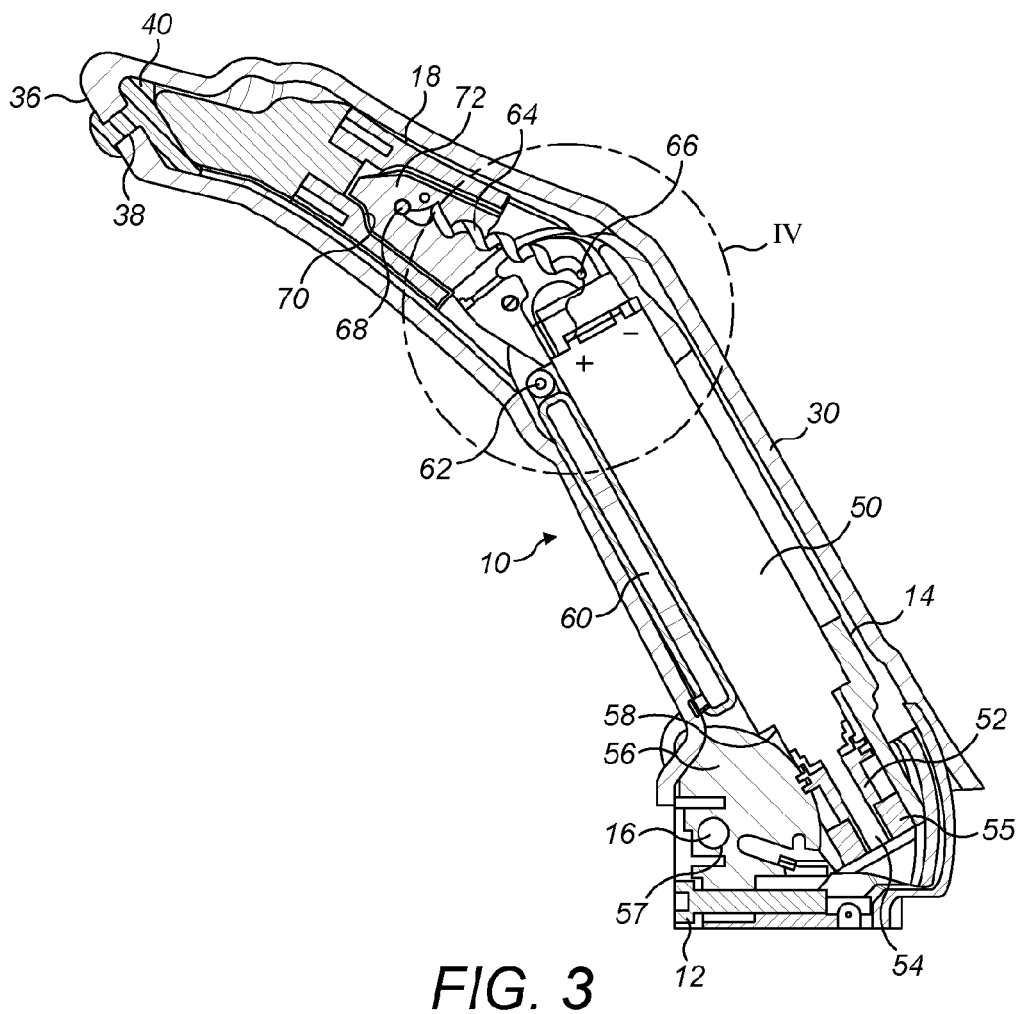
FIG. 3 is a section view of the digit along the line shown in FIG. 2.

FIG. 2 shows the same view of the digit 10 as in FIG. 1, but the digit 10 has now been covered by a cover 30. The cover 30 has a proximal end 32 which is open and a remote end 34 which is closed. The cover 30 is preferably formed as a single piece from an elastomer, and the internal surface of the cover may be at least partly coated in polyurethane to allow the cover 30 to more easily slip on and off the digit 10. The remote end 34 of the cover 30 has a tip 36 which corresponds with the digit tip 22 beneath. The tip 36 has at least one aperture 38 which extends all the way through the cover 30. A conductive adhesive 40 is injected through the aperture(s) 38 so that a portion of the adhesive adheres to the internal surface of the cover 30 adjacent the tip 36. As best shown in FIG. 3, the adhesive 40 extends from the internal surface of the cover 30 outwards through the aperture(s) 38 and a portion is also left upon the external surface of the cover 30 at the tip 36. A non-limiting example of a conductive adhesive suitable for this purpose is "Kembond SNG-RTV" sold by Kemtron Limited of Braintree, United Kingdom. This particular product is an electrically conductive adhesive comprising nickel graphite particles within a silicon resin.

FIG. 3 is a sectional view of the digit 10 and cover 30 taken along the line shown in FIG. 2. This view shows more details of the operating components of the digit 10 as well as the conductive path from the tip of the cover 30. Located within the interior of the first digit member 14 is a motor 50, which is operable to drive a worm gear 52 located on a drive shaft 54 extending from the motor 50. A bearing 55 is positioned at the distal end of the drive shaft 54. A worm gear wheel 56 is fixedly mounted on the base member 12, and the digit 10 extends generally tangentially with respect to the worm gear wheel 56 and is mounted for rotation about the worm gear wheel 56. The first digit member 14 is connected to the worm gear wheel 56 via the pivot rod 16 which passes through a circular aperture 57 in the worm gear wheel 56, thereby forming a first joint about rotational axis A. The worm gear 52 is in engagement with the worm gear wheel 56 such that, when the motor 50 is operated in use of the digit 10, the first digit member 14 rotates about the worm gear wheel 56.

It can also be seen in FIG. 3 that the first digit member 14 is coupled to the second digit member 18 by a coupling mechanism, which is arranged such that when the first digit member 14 rotates about the worm gear wheel 56, the second digit member 18 pivots with respect to the first digit member 14. The coupling mechanism includes one or more cables 60, which are connected between a coupling pin 62 on the second digit member 18 and the worm gear wheel 56 or base member 12. As a result, when the first digit member 14 pivots with respect to the worm gear wheel 56, the one or more cables 60 pull on the coupling pin 62 and move the second digit member 18 towards the worm gear wheel 56, i.e. a movement which mimics the closing of a finger of a human hand.

A biasing member 64 has a first end connected to the first digit member 14 by a first biasing pin 66, and a second end connected to the second digit member 18 by a second biasing pin 68. The biasing member 64 consequently spans the joint between the first and second digit members 14,18 and is offset from a longitudinal axis of the digit 10 such that it biases the second digit member 18 into alignment with the first digit member 14, i.e. towards an extended position away from the aforementioned closed position.

The biasing member 64 could be connected into the first and second digit members 14,18 in a number of ways. In the illustrated embodiment the proximal end of the second digit member 18 contains a hollow chamber 70, whose internal surface is coated with the same conductive paint or coating as the front face 28 of the second digit member 18. The first end of the biasing member 64 is connected into a plastic insert 72 by the first biasing pin 66. The external surface of the insert 72 is also coated with the conductive paint or coating. The insert 72 is threaded or otherwise fixed into the chamber 70 to provide the connection between the first end of the biasing member 64 and the second digit member 18, as well as a conductive path from the second digit member 18 to the biasing member 64.

Figure 4:
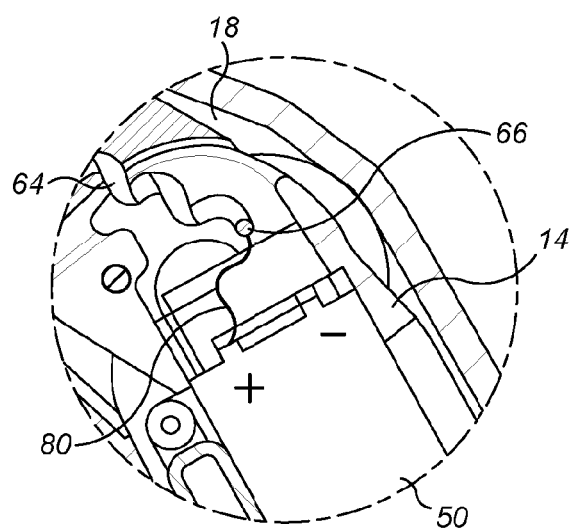
FIG. 4 is a detail view of the section marked IV in FIG. 3.

As can be seen in the detail view of FIG. 4, the first biasing pin 66 is connected to the positive terminal of the motor 50 by a wire connector 80. The wire connector 80 has a degree of slack so as to allow the second digit member 18 to pivot relative to the first digit member 14 without the wire connector 80 being pulled taut or being strained in any way. In this way the wire connector 80 continues the conductive path from the first end of the biasing member 64 to a casing 58 of the motor 50 or alternatively to the support member 12.

The first digit member 14 may include at least one electrical contact member (not shown) and the worm gear wheel 56 may include at least one electrical contact surface (not shown). The electrical contact member and the electrical contact surface are used to supply electrical power to the motor 50 and may also act as part of the conductive path. The electrical contact member is connected to the terminal inputs of the motor 50 via electrical wires (not shown). The electrical contact surface is connected to an electrical power source which is located in the main body of the prosthesis (not shown). The electrical contact member and the electrical contact surface are arranged to slidably contact one another as the first digit member 14 rotates about the worm gear wheel 56. The electrical contact member(s) may comprise, for example, pin members, brushes or sprung contacts.

As described above, the electrical contact members and the electrical contact surfaces are used to supply electrical power to the motor 50. The electrical contact surfaces may provide AC or DC electrical power to the motor 50 via the electrical contact members.

INDUSTRIAL APPLICABILITY

The manner in which the digit operates a touchscreen device will now be described. The hand prosthesis of which the digit 10 forms part will comprise an electronic device (not shown), which is configured to control the operation of the motor 50. The electronic device may be located within the main body of the prosthesis.

The motor 50 is operable via one or more switches (not shown). The switches may be actuated by residual movement, or wrist and/or shoulder movement of the wearer of the hand prosthesis, or the like. Alternatively, or additionally, the motor 50 may be operable via signals derived from the activity of, or from, electromyographic (EMG) activity of residual muscle actions of the wearer, pressure sensitive resistors on the wearer, signals derived from one or more neural implants in the wearer, EMG activity from reinnervated muscles, muscles of the feet and/or chest, or the like. The electronic device is configured to process the actuation signals from the wearer to operate the motor 50.

In use the wearer provides a movement signal, for example, an EMG signal, to operate the motor 50. When the motor 50 receives the signal, via the electronic device, the drive shaft 54 is rotated in a chosen direction. This causes the worm gear 52 to rotate and rotate the first digit member 14 about the worm gear wheel 56. Depending on the EMG signal and hence the direction of rotation of the drive shaft 54, the first digit member 14 rotates about the worm gear wheel 56 with both the first digit member and second digit member 18 closing in a hand grasping action, or the first digit member and second digit member opening in a hand extension action.

When the wearer wishes to operate a touchscreen device, they may choose to extend the digit 10 into a "pointing" position, or to the slightly bent configuration shown in FIG. 3. In order to operate the screen of the device, the tip 36 of the cover 30 is brought into contact with the desired area of the screen. In doing so, the portion of the conductive adhesive 40 left upon the external surface of the tip 36 comes into contact with the screen. This causes a change in capacitance to be registered by the capacitive resistance screen of the device due to the conductive path which passes through the aperture 38 in the cover along the adhesive 40. Once inside the cover 30, the path passes from the adhesive 40 to the conductive paint 26 which runs from the tip 22 of the second digit member 18 down the front face 28 of the second digit member 18.

As best seen in FIG. 3, the conductive paint 26 extends to the proximal end 19 of the second digit member 18 and then internally to the chamber 70 and plastic insert 72. As the facing surfaces of both the chamber 70 and insert 72 are also coated with the paint 26, the conductive path extends from the exterior of the second digit member 18 to the insert 72. From there, it runs onto the second biasing pin 68 and from the second digit member 18 to the first digit member 14 via the biasing member 64. The path then passes from the biasing member 64 to the wire connector 80 via the first biasing pin 66. The path then extends to the outer casing of the motor 50.

The present invention provides a digit for a prosthetic hand which means a wearer who still has one hand does not need to use their remaining hand to operate a touchscreen device. It also provides a more consistent contact and change in capacitance than previous proposals which rely upon a metal pad or dome at the tip of the digit. Providing a conductive substance on the elastomeric cover also avoids scratching and cracking of the touchscreen compared with such metal contact pads. The present invention also provides a consistent conductive path through the digit without any likelihood of the path being broken or intermittent due to repeated movements of the first and second digit members or due to exposed conductive wires which may be fouled or damaged during use of the digit/prosthesis.

Whilst the preferred digit described above is formed from a base member and first and second digit members, the digit of the present invention may be formed from a single digit member which is pivotably connected to a base member. In such a case the digit tip and its optional cover would be at the remote end of the single digit member from the base member.

Whilst it may be preferred to cover the digit, or at least the tip thereof, with a cover to protect against damage and ingress of dirt and other undesired substances, the cover is not an essential component of the present invention. In the absence of a cover, the first conductive substance may be applied to the digit tip directly along with the second conductive substance.

When a cover is employed it may have a plurality of apertures extending through the cover rather than the single aperture shown in the illustrated embodiment. As in the illustrated embodiment conductive adhesive or another conductive substance is injected through each aperture so that adhesive adheres to the internal surface of the cover adjacent the tip. The adhesive extends from the internal surface of the cover outwards through the apertures and a portion is also left upon the external surface of the cover at the tip.

Whilst the first conductive substance is a conductive adhesive in the preferred embodiment, it may alternatively be a conductive paint, a conductive coating or a conductive film. Similarly, whilst the second conductive substance is a conductive paint in the preferred embodiment, it may alternatively be a conductive adhesive, a conductive coating or a conductive film. Whilst the first and second substances are preferably different substances, they may alternatively be the same substance. In the case of a conductive film, the film may incorporate a length of a conductor so as to form a conductive track or path, or alternatively the conductor may be sandwiched between two layers of film.

Whilst the conductive path of the preferred example of the digit described herein is defined by applying the conductive substance to a limited region of the or each digit member, the entire digit member(s) may be covered with the conductive substance such that the conductive path from the digit tip is not limited to a single track of the conductive substance. In this instance the entire digit member(s) would act as the conductive path.

As stated above, the present invention encompasses non-powered digits as well as the powered digit of the preferred embodiment. In the case of a non-powered digit the conductive path defined by the conductive substance(s) may be extended by additional conductive substance(s) or a connector wire.

These and other modifications and improvements may be incorporated without departing from the scope of the present invention.

The invention claimed is:

1. A digit for a prosthetic hand, the digit comprising:
a base member attachable to the hand;
a first of at least two digit members pivotably connected to the base member, the first digit member comprising a motor comprising electrical contacts; and a second of the at least two digit members
wherein the second digit member has a digit tip remote from the base member, and the second digit member is at least partially covered with at least one conductive substance which defines a conductive path which leads from the digit tip towards the base member and which path is in electrical contact with one of the electrical contacts of the motor.

2. The digit of claim 1, wherein the at least one conductive substance is selected from the group comprising of: a conductive adhesive, a conductive paint and a conductive coating.

3. The digit of claim 1, wherein the at least one conductive substance includes a first conductive substance and a second conductive substance directly adjacent the first conductive substance, the first and second conductive substances defining a portion of the conductive path.

4. The digit of claim 3, wherein the first conductive substance is a conductive adhesive, and the second conductive substance is a conductive paint.

5. A digit for a prosthetic hand, the digit comprising:
a base member attachable to the hand;
a first of at least two digit members pivotably connected to the base member, and a second of the at least two digit members a digit tip remote from the base member, and being at least partially covered with a cover adapted to fit over at least the digit tip, the cover having a cover tip which lies over the digit tip when the cover is in place, the cover comprising at least one conductive substance which defines a conductive path which leads from the digit tip towards the base member, to an electrical contact of a motor contained within the first digit member
wherein the cover tip includes at least one aperture extending through the cover, and the at least one conductive substance is provided on an exterior of the cover tip and within the at least one aperture such that it defines part of the conductive path from the exterior of the cover tip to the digit tip.

6. A digit for a prosthetic hand, the digit comprising:
a base member attachable to the hand;
a first of at least two digit members pivotably connected to the base member; and a second of the at least two digit members pivotably connected to the first digit member;
wherein the second of the at least two digit members has a digit tip remote from the base member, and the second digit member is at least partially covered with at least one conductive substance which defines a conductive path which leads from the digit tip towards the base member, and:
wherein the digit for the prosthetic hand further comprises a biasing member having a first end connected to the first digit member and a second end connected to the second digit member, the biasing member biasing the second digit member towards substantial alignment with the first digit member;

and wherein the biasing member extends the conductive path from the second digit member to an electrical contact of a motor contained within the first digit member.

7. The digit of claim 6, wherein the digit for the prosthetic hand is a powered digit and the motor is contained within a motor casing, and the digit for the prosthetic hand further comprising a conductive wire having a first end connected to the first end of the biasing member, and a second end connected to the motor casing.

* * * * *

UNITED STATES PATENT AND TRADEMARK OFFICE
CERTIFICATE OF CORRECTION

| | | |
|---|---|---|
| PATENT NO. | : 9,999,522 B2 | Page 1 of 1 |
| APPLICATION NO. | : 15/120784 | |
| DATED | : June 19, 2018 | |
| INVENTOR(S) | : Hugh Gill | |

It is certified that error appears in the above-identified patent and that said Letters Patent is hereby corrected as shown below:

On the Title Page

Column 1, Item (*), Line 3, under Notice 3, after "0 days." delete "days.".

In the Specification

In Column 4, Line 62, after "line" insert --III-III--.

In the Claims

In Column 8, Line 11, Claim 1, change "members" to --members,--.

In Column 8, Line 20, Claim 1, change "comprising" to --consisting--.

In Column 8, Line 41, Claim 5, change "member," to --member--.

In Column 8, Line 43, Claim 5, change "member" to --member,--.

In Column 8, Line 61, Claim 6, change "and:" to --and--.

In Column 8, Line 67, Claim 6, change "member;" to --member,--.

Signed and Sealed this
Seventh Day of April, 2020

Andrei Iancu
*Director of the United States Patent and Trademark Office*